United States Patent [19]
Alaimo et al.

[11] 4,222,948
[45] Sep. 16, 1980

[54] [[(4-AMINOPHENYL)SULFONYL]AMINO]-PHENYL PHOSPHORODIAMIDATES

[75] Inventors: Robert J. Alaimo; James B. Sheffer; Ozra E. Millner, Jr., all of Norwich, N.Y.

[73] Assignee: Morton-Norwich Products, Inc., Norwich, N.Y.

[21] Appl. No.: 65,934

[22] Filed: Aug. 13, 1979

[51] Int. Cl.$^2$ ............................................. C07C 143/80
[52] U.S. Cl. .............................. 260/397.7 R; 424/211; 424/228
[58] Field of Search .................................. 260/397.7 R

[56] References Cited
U.S. PATENT DOCUMENTS

| 2,245,539 | 6/1941 | Warnat | 260/397.7 R |
| 4,032,601 | 6/1977 | Birum | 260/969 |

FOREIGN PATENT DOCUMENTS 131444  2/1949  Australia ........................... 260/397.7 R

OTHER PUBLICATIONS

Li et al., Chem. Abstracts, vol. 52, Col. 14552 (1958) (abst. of Li et al., Hua Hseuh Hseuh Pao, vol. 23, pp. 99–104 (1957).
Meltzer et al., Chem. Abstracts, vol. 59, Col. 11341 (1963).

Primary Examiner—John D. Randolph
Attorney, Agent, or Firm—Anthony J. Franze

[57] ABSTRACT

[[(4-Aminophenyl)sulfonyl]amino]phenyl phosphorodiamidates are useful as inhibitors of the enzyme urease as well as being effective antimicrobial agents.

4 Claims, No Drawings

[[(4-AMINOPHENYL)SULFONYL]AMINO]PHENYL PHOSPHORODIAMIDATES

This invention is concerned with chemical compounds. More particularly, it is concerned with compounds of the formula:

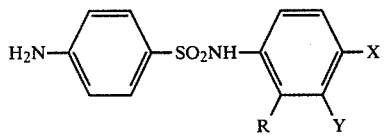

wherein X and Y are dissimilar substituents selected from hydrogen and

and R is hydrogen or methyl.

These compounds are potent inhibitors of the enzyme urease. Urease is produced by a number of bacterial species particularly Proteus exemplary of which are *Proteus mirabilis, Proteus vulgaris, Proteus morganii* and *Proteus rettgeri,* all of which are well-known urinary tract pathogens. Their ability to produce urease in the urinary tract, which contains substantial amounts of urea, provides a setting wherein urease splits urea according to this scheme:

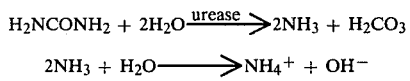

The reaction sequence poses a hyperammonuria and alkalinity of the urine affording a locale favorable to the formation of struvite ($MgNH_4PO_4.6H_2O$) a predominant component of infected urinary calculi. Such struvite formation and alkalinization of the urine render the treatment of urinary tract infections difficult and oftentimes recalcitrant to otherwise effective urinary tract antiseptics.

The members of this series of compounds of this invention are highly effective in inhibiting urease which is intimately associated with the pathogenicity of the Proteus species of bacteria. Thus, a concentration of members of this series in the range of $2 \times 10^{-7}$ to $4 \times 10^{-7}$ molar evinces a 50% inhibition of the urease of intact *Proteus mirabilis* cells.

The anti-urease potency of the compound of this invention was determined using intact *Proteus mirabilis* cells as the source of urease. Compounds were preincubated with *Proteus mirabilis* cells suspended in a saline solution (0.1 molar) buffered with 0.1 molar tris(hydroxymethyl)aminomethane (pH 8.0). After 40 minutes preincubation, the remaining urease activity was determined by collecting the ammonia formed in five minutes after the addition of the substrate, urea. Ammonia assays were carried out according to the procedure of Seligson and Seligson [*J. Lab. Clin. Med.* 38, 324-330 (1951)]. Percent inhibition was calculated by comparing the amount of ammonia generated by cells preincubated with compounds of this series with the controls, in which preincubation was carried out in the absence of compound.

The members of this series of compounds of this invention posses antibacterial activity. They are particularly inimical to *Proteus mirabilis* and *Escherichia coli* at levels of 2.0 to $9.4 \times 10^{-5}$ molar in the commonly employed in vitro technique for determining antibacterial activity.

The antibacterial property of these compounds as well as their urease inhibitory action make them useful in combatting infections of the urinary tract.

In order that this invention may be fully available to and understood by those skilled in the art, the following procedures are supplied.

EXAMPLE I

3[[(4-Aminophenyl)sulfonyl]amino]phenyl Phosphorodiamidate

A. 3-[(4-Nitrophenyl)sulfonyl]aminophenol

A mixture of 3-aminophenol (33 g, 0.3 mole) and p-nitrobenzenesulfonyl chloride (66 g, 0.3 mole) in pyridine (350 ml) was heated at 80° on a steam bath for 4 hours. The reaction mixture was poured on ice and acidified with acetic acid. The precipitated product was filtered and recrystallized from isopropanol and gave 50 g (49%) of product which was used in Part B.

B. 3-[(4-Nitrophenyl)sulfonyl]aminophenyl Phosphorodiamidate

A mixture of 30 g (0.1 mole) of 3-[(4-nitrophenyl)sulfonyl]-aminophenol and aluminum chloride (½g) in phosphorous oxychloride (400 ml) was heated under reflux with stirring for 4 hours. The excess $POCl_3$ was removed in vacuo and the residue flushed several times with chloroform. The residue was suspended in $CHCl_3$ (500 ml) and $NH_3$ bubbled into the stirred mixture for 30 minutes at $-10°$. The product was removed by filtration, washed with chloroform, ether and air dried. The crude material was suspended in water (500 ml) and acidified with acetic acid. Filtration gave crude product which was purified by recrystallization from isopropanol-ether. The white product 28 g (76%) was used in Part C.

C. 3-[[(4-Aminophenyl)sulfonyl]amino]phenyl Phosphorodiamidate

A methanol solution (350 ml) of 3-[(4-nitrophenyl)-sulfonyl]-aminophenyl phosphorodiamidate (17 g, 0.045 mole) was hydrogenated over 5% Pd/C catalyst at 40 psi. Theoretical $H_2$ pick up took 1.5 hours. The catalyst was removed by filtration and the solvent removed in vacuo. The residue was recrystallized from isopropanolether and gave 14 g (91%). Recrystallized from isopropanol-methanol gave white solid, m.p. 185°-186°.

Anal. Calcd. for $C_{12}H_{15}N_4O_4SP$: m.w. 342.32 C, 42.11; H, 4.42; N, 16.37. Found: C, 42.47; H, 4.19; N, 16.49.

EXAMPLE II

4-[[(4-Aminophenyl)sulfonyl]amino]phenyl Phosphorodiamidate

A. 4-[(4-Nitrophenyl)sulfonyl]aminophenol

A mixture of 4-aminophenol (27 g, 0.25 mole) and 4-nitrobenzenesulfonyl chloride (55 g, 0.25 mole) in pyridine (500 ml) was heated under reflux for 4 hours.

The reaction mixture was poured in ice water and acidified with acetic acid. The crude product weighed 86 g. Recrystallization from $CH_3NO_2$ provided 53 g (73%) of material used in Part B; m.p. 197°–198°.

Anal. Cald. for $C_{12}H_{10}N_2O_5S$: m.w. 296.30 C, 48.98; H, 3.43; N, 9.52. Found: C, 48.96; H, 3.37; N, 9.44.

B. 4-[(4-Nitrophenyl)sulfonyl]aminophenyl Phosphorodiamidate

A mixture of the phenol from Part A (38 g, 0.13 mole) and $AlCl_3$ (1 g) in $POCL_3$ (500 ml) was heated under reflux for 4 hours. The excess $POCL_3$ was removed in vacuo and the residue flushed with $CHCl_3$. The crude product was suspended in $CHCl_3$ (500 ml) and $NH_3$ bubbled into the mixture at $-10°$ for 30 minutes. the product was filtered off and washed with $CHCl_3$ and ether. The solid was suspended in $H_2O$ and acidified with HOAc. The precipitated product weighed 44 g (91%). Recrystallization from $CH_3OH$—$CH_3NO_2$ provided a product that was used in Part C.

C. 4-[[(4-Aminophenyl)sulfonyl]amino]phenyl Phosphorodiamidate

To 7.5 g (0.02 mole) of the nitro compound from Part B was added 300 ml of $CH_3OH$ and Pd/C catalyst. The mixture was hydrogenated at 40 psi. The solvent was removed in vacuo and the residue stirred in isopropanol and ether. Yield of white solid 6 g (88%). Recrystallization from isopropanol-methanol gave analytical material which melted at 174°–175°.

Anal. Cald. for $C_{12}H_{15}N_4O_4PS$: C, 42.11; H, 4.42; N, 16.37. Found: C, 42.34; H, 4.52; N, 16.40.

EXAMPLE III

4-[[(4-Aminophenyl)sulfonyl]amino]-3-methylphenyl Phosphorodiamidate

A. 4-[[(4-Nitrophenyl)sulfonyl]amino]-3-methylphenol

To a stirred mixture of 4-amino-3-methylphenol (24 g, 0.2 mole) in 600 ml of pyridine was added all at once p-nitrobenzenesulfonyl chloride (Eastman) (45 g, 0.2 mole) followed by heating on a steam bath for 2 hours. The dark oily solution was poured into 4 liters of water and then treated with glacial acetic acid until acid. The tar crystallized on standing to give after filtration 67 g (100%) of brown solid. The entire sample was recrystallized from $CH_3NO_2$ to give 52 g of pure intermediate.

B. 4-[[(4-Nitrophenyl)sulfonyl]amino]-3-methylphenyl Phosphorodiamidate

A stirred mixture of 4-[[(4-nitrophenyl)sulfonyl]amino]-3-methylphenol (51 g, 0.15 mole) and 800 ml of phosphorus oxychloride with a catalytic amount of aluminum chloride was heated at reflux for 4 hours. The reaction mixture was concentrated in vacuo followed by flushing with chloroform. The brown oil residue was treated with 1 liter of fresh chloroform maintained at 0° with a dry ice/acetone bath. Ammonia was added to the cold stirred solution below the surface. The gas addition was stopped after 1 hour and the reaction mixture allowed to warm to room temperature. The reaction mixture was filtered to give a light yellow solid. The solid was treated with 3 liters of water followed by filtration. The gray solid was recrystallized from $CH_3NO_2$; yield 7 g (11%). The intermediate was used in Part C without further purification.

4-[[4-Aminophenyl)sulfonyl]amino]-3-methylphenyl Phosphorodiamidate

A mixture of 4-[[(4-nitrophenyl)sulfonyl]amino]-3-methylphenyl phosphorodiamidate (7 g, 0.02 mole) in 250 ml of methanol was hydrogenated on Parr apparatus using 5% palladium on carbon 50% water wet catalyst. The reduction stopped (100% theory) after 1 hour and the catalyst removed by filtration. The filtrate remaining was concentrated in vacuo followed by trituration with isopropanol to give an off-white solid 5 g (78%).

An analytical sample was prepared after on recrystallization from ethanol, m.p. 191–195 corr.

Anal. Calcd. for $C_{13}H_{17}N_4O_4PS$: C, 43.82; H, 4.81; N, 15.72. Found: C, 43.42; H, 4.64; N, 15.58.

What is claimed is:

1. A compound of the formula:

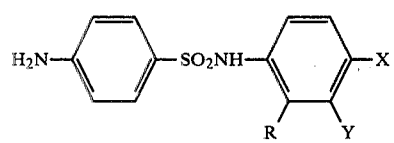

wherein X and Y are dissimilar substituents selected from hydrogen and

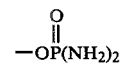

and R is hydrogen or methyl.

2. The compound 3-[[(4-aminophenyl)sulfonyl]amino]phenyl phosphorodiamidate.
3. The compound 4-[[(4-aminophenyl)sulfonyl]amino]phenyl phosphorodiamidate.
4. The compound 4-[[(4-aminophenyl)sulfonyl]amino]-3-methylphenyl phosphorodiamidate.

* * * * *